US006777000B2

(12) United States Patent
Ni et al.

(10) Patent No.: US 6,777,000 B2
(45) Date of Patent: Aug. 17, 2004

(54) IN-SITU GEL FORMATION OF PECTIN

(75) Inventors: Yawei Ni, College Station, TX (US); Kenneth M. Yates, Grand Prairie, TX (US)

(73) Assignee: Carrington Laboratories, Inc., Irving, TX (US)

( * ) Notice: Subject to any disclaimer, the term of this patent is extended or adjusted under 35 U.S.C. 154(b) by 148 days.

(21) Appl. No.: 09/795,897

(22) Filed: Feb. 28, 2001

(65) Prior Publication Data

US 2002/0119941 A1 Aug. 29, 2002

(51) Int. Cl.[7] .......................... A01K 9/14; A01N 61/00; A01N 43/04
(52) U.S. Cl. .............................. 424/488; 514/1; 514/2; 514/44; 514/157
(58) Field of Search ........................ 514/1, 2, 44, 157; 424/488

(56) References Cited

U.S. PATENT DOCUMENTS

| | | | | |
|---|---|---|---|---|
| 3,927,205 A | * | 12/1975 | Ohno et al. | 514/772.5 |
| 3,973,051 A | * | 8/1976 | Buckley et al. | 426/574 |
| 3,982,003 A | | 9/1976 | Mitchell et al. | |
| 4,199,560 A | | 4/1980 | Gyarmati et al. | |
| 4,305,933 A | | 12/1981 | Wiczer | |
| 4,500,510 A | | 2/1985 | Goldstein | |
| 4,529,613 A | * | 7/1985 | Mezzino et al. | 426/590 |
| 4,613,500 A | | 9/1986 | Suzuki et al. | |
| 4,652,441 A | | 3/1987 | Okada et al. | |
| 4,711,782 A | | 12/1987 | Okada et al. | |
| 4,725,438 A | | 2/1988 | Leazer | |
| 4,842,866 A | | 6/1989 | Horder et al. | |
| 4,847,091 A | | 7/1989 | Illum | |
| 4,917,890 A | | 4/1990 | McAnalley | |
| 4,917,893 A | | 4/1990 | Okada et al. | |
| 4,925,677 A | | 5/1990 | Feijen | |
| 4,981,875 A | | 1/1991 | Leusner et al. | |
| 5,059,189 A | | 10/1991 | Cilento et al. | |
| 5,061,492 A | | 10/1991 | Okada et al. | |
| 5,064,650 A | | 11/1991 | Lew | |
| 5,071,644 A | | 12/1991 | Viegas et al. | |
| 5,079,018 A | | 1/1992 | Ecanow | |
| 5,147,648 A | | 9/1992 | Bannert | |
| 5,188,825 A | | 2/1993 | Iles et al. | |
| 5,192,802 A | | 3/1993 | Rencher | |
| 5,204,108 A | | 4/1993 | Illum | |
| 5,208,031 A | | 5/1993 | Kelly | |
| 5,238,917 A | | 8/1993 | Fujii et al. | |
| 5,266,318 A | | 11/1993 | Taylor-McCord | |
| 5,284,659 A | | 2/1994 | Cherukuri et al. | |
| 5,288,498 A | | 2/1994 | Stanley et al. | |
| 5,288,500 A | | 2/1994 | Ibsen | |
| 5,314,915 A | | 5/1994 | Rencher | |
| 5,318,780 A | | 6/1994 | Viegas et al. | |
| 5,362,424 A | | 11/1994 | Lee et al. | |
| 5,409,703 A | | 4/1995 | McAnalley et al. | |
| 5,435,997 A | | 7/1995 | Burns | |

FOREIGN PATENT DOCUMENTS

| | | |
|---|---|---|
| WO | WO 98/47535 | 4/1998 |
| WO | WO 98/47535 | 10/1998 |
| WO | WO 99/27905 | 6/1999 |

OTHER PUBLICATIONS

Eck and Wilson (In Goodman and Gilman's Pharmacological basis of Therapeutics, McGraw–Hill publishers, 1995, see p. 81, col. 2, through p. 82, col. 2).*

Verma et al (Nature 389: 239–242, 1997).*

Anderson (Nature 392:25–30, 1998).*

Romano et al (Stem Cells 18: 19–39, 2000).*

Somia and Verma (Nature Reviews Genetics 1: 91–99, 2000).*

Austin et al., "The Effect of Calcium Pectinate Gel Implants on the Healing of Experimental Defects in the Femora of Albino Rats," *S. Afr. J. Med. Sci.*, 38:55–60 (1973).

Sriamornsak et al., "Calcium pectinate gel beads for controlled release drug delivery: II. Effect of formulation and processing variables on drug release," *J. Microencapsulation*, 16(3):303–313 (1999).

Sriamornsak et al., "Development of sustained release theophylline pellets coated with calcium pectinate," *J. of Controlled Release*, 47:221–232 (1997).

Ashford et al., "Studies on Pectin Formulations for Colonic Drug Delivery," *Journal of Controlled Release*, 30:225–232 (1994).

Aydin et al., Preparation and Evaluation of Pectin Beads, *Int'l Journal of Pharmaceutics*, 137:133–136 (1996).

Garnier et al., "Selectivity and Cooperativity in the Binding of Calcium Ions by Pectins," *Carbohydrate Research*, 256:71–81 (1994).

Garnier et al., "Phase Diagrams of Pectin—Calcium Systems: Influence of pH, Ionic Strength, and Temperature on the Gelation of Pectins with Different Degrees of Methylation," *Carbohydrate Research*, 240:219–232 (1993).

Mandal et al., "Structure of the $_D$–Galactan Isolated From Aloe barbadensis Miller*," *Carbohydrate Research*, 86:247–257 (1980).

Mandal et al., "Characterisation of Polysaccharides of Aloe Barbadensis Miller: Part III—Structure of an Acidic Oligosaccharide," *Indian Journal of Chemistry*, 22(b):890–893 (1983).

(List continued on next page.)

*Primary Examiner*—Dave T. Nguyen
*Assistant Examiner*—Richard Schnizer
(74) *Attorney, Agent, or Firm*—Needle & Rosenberg, P.C.

(57) ABSTRACT

In-situ gelation of a pectic substance. Composition, method of preparation, and method of use of a pectin in-situ gelling formulation for the delivery and sustained release of a physiologically active agent to the body of an animal. The pectin can be isolated from Aloe vera.

47 Claims, 5 Drawing Sheets

(List continued on next page.)

U.S. PATENT DOCUMENTS

| | | | |
|---|---|---|---|
| 5,503,822 | A | 4/1996 | Schulman |
| 5,505,966 | A | 4/1996 | Edman et al. |
| 5,508,043 | A | 4/1996 | Krishnamurthy |
| 5,512,306 | A | 4/1996 | Carlsson et al. |
| 5,525,634 | A | 6/1996 | Sintov et al. |
| 5,545,673 | A | 8/1996 | Kelly |
| 5,571,531 | A | 11/1996 | McDermott et al. |
| 5,578,307 | A | 11/1996 | Wunderlich et al. |
| 5,587,175 | A | 12/1996 | Viegas et al. |
| 5,599,551 | A | 2/1997 | Kelly |
| 5,622,717 | A | 4/1997 | Fuisz |
| 5,639,795 | A | 6/1997 | Friedman et al. |
| 5,645,827 | A | 7/1997 | Marlin et al. |
| 5,648,399 | A | 7/1997 | Friedman et al. |
| 5,651,987 | A | 7/1997 | Fuisz |
| 5,674,495 | A | 10/1997 | Bowersock et al. |
| 5,707,644 | A | 1/1998 | Illum |
| 5,612,053 | A | 4/1998 | Baichwal et al. |
| 5,738,865 | A | 4/1998 | Baichwal et al. |
| 5,760,102 | A | 6/1998 | Hall et al. |
| 5,770,582 | A | 6/1998 | von Borstel et al. |
| 5,804,212 | A | 9/1998 | Illum |
| 5,811,123 | A | 9/1998 | Fuisz |
| 5,840,332 | A | 11/1998 | Lerner et al. |
| 5,849,327 | A | 12/1998 | Berliner et al. |
| 5,866,619 | A | 2/1999 | Sintov et al. |
| 5,900,238 | A | 5/1999 | Gombotz et al. |
| 5,902,796 | A | 5/1999 | Shand et al. |
| 5,929,051 | A * | 7/1999 | Ni ............................... 514/54 |
| 5,935,604 | A | 8/1999 | Illum |
| 5,942,242 | A | 8/1999 | Mizushima et al. |
| 5,948,749 | A | 9/1999 | Igarashi et al. |
| 5,958,443 | A | 9/1999 | Viegas et al. |
| 6,033,651 | A | 3/2000 | Dolak et al. |
| 6,060,078 | A | 5/2000 | Lee |
| 6,063,915 | A | 5/2000 | Hansen et al. |
| 6,083,531 | A | 7/2000 | Humbert-Droz et al. |
| 6,083,540 | A | 7/2000 | Christensen et al. |
| 6,103,269 | A | 8/2000 | Wunderlich et al. |
| 6,133,440 | A | 10/2000 | Qiu et al. |
| 6,136,334 | A | 10/2000 | Viegas et al. |
| 6,139,880 | A | 10/2000 | Dolak et al. |
| 6,149,940 | A | 11/2000 | Maggi et al. |
| 6,159,491 | A | 12/2000 | Durrani |
| 6,171,594 | B1 | 1/2001 | Nielsen |
| 6,174,549 | B1 | 1/2001 | Greenshields et al. |
| 6,197,327 | B1 | 3/2001 | Harrison et al. |
| 6,197,346 | B1 | 3/2001 | Mathiowitz et al. |
| 6,210,710 | B1 | 4/2001 | Skinner |
| 6,217,908 | B1 | 4/2001 | Mathiowitz et al. |
| 6,228,387 | B1 | 5/2001 | Borod |
| 6,228,396 | B1 | 5/2001 | Watts |
| 6,231,888 | B1 | 5/2001 | Lerner et al. |
| 6,248,360 | B1 | 6/2001 | Choi et al. |
| 6,261,574 | B1 | 7/2001 | Costello |
| 6,274,548 | B1 * | 8/2001 | Ni ............................... 514/2 |
| 6,284,273 | B1 | 9/2001 | Lenaerts et al. |
| 6,290,964 | B1 | 9/2001 | Shupe et al. |
| 6,309,675 | B1 | 10/2001 | Sobczak |
| 6,310,089 | B1 | 10/2001 | Watts et al. |
| 6,313,103 | B1 | 11/2001 | Ni et al. |
| 6,333,194 | B1 | 12/2001 | Levy et al. |
| 6,342,251 | B1 | 1/2002 | Illum et al. |
| 6,350,469 | B1 | 2/2002 | Daggy et al. |
| 6,355,276 | B1 | 3/2002 | Illum et al. |
| 6,358,525 | B1 | 3/2002 | Guo et al. |
| 6,365,200 | B1 | 4/2002 | Birnholz et al. |
| 6,365,624 | B1 | 4/2002 | Davidson et al. |
| 6,368,639 | B1 | 4/2002 | Farooqui et al. |
| 6,375,963 | B1 | 4/2002 | Repka et al. |
| 6,375,988 | B1 | 4/2002 | Suzuki et al. |
| 6,383,495 | B1 | 5/2002 | Ramakrishna et al. |
| 6,383,513 | B1 | 5/2002 | Watts et al. |
| 6,387,394 | B1 | 5/2002 | Baichwal et al. |
| 6,387,408 | B1 | 5/2002 | Illum et al. |
| 6,387,917 | B1 | 5/2002 | Illum et al. |
| 6,391,318 | B1 | 5/2002 | Illum et al. |
| 6,413,494 | B1 | 7/2002 | Lee et al. |
| 6,413,941 | B1 | 7/2002 | Garnett et al. |
| 6,416,779 | B1 | 7/2002 | D'Augustine et al. |
| 6,423,345 | B2 | 7/2002 | Bernstein et al. |
| 6,432,440 | B1 | 8/2002 | Watts et al. |
| 6,436,461 | B1 | 8/2002 | Bouwmeesters et al. |
| 6,451,351 | B1 | 9/2002 | Kawashima et al. |
| 6,455,066 | B1 | 9/2002 | Fischer et al. |
| 6,465,626 | B1 | 10/2002 | Watts et al. |
| 6,475,526 | B1 | 11/2002 | Smith |
| 6,517,868 | B2 | 2/2003 | Fassihi et al. |
| 6,531,152 | B1 | 3/2003 | Lerner et al. |
| 6,534,065 | B1 | 3/2003 | Makin et al. |
| 6,541,035 | B1 | 4/2003 | Pallado et al. |
| 6,551,631 | B2 | 4/2003 | Shupe et al. |
| 6,552,024 | B1 | 4/2003 | Chen et al. |
| 6,558,792 | B1 | 5/2003 | Vaabengaard et al. |
| 6,562,363 | B1 | 5/2003 | Mantelle et al. |
| 6,569,463 | B2 | 5/2003 | Patel et al. |
| 6,582,728 | B1 | 6/2003 | Platz et al. |
| 6,596,297 | B2 | 7/2003 | Neurath et al. |
| 2001/0046519 | A1 | 11/2001 | Illum et al. |
| 2002/0009418 | A1 | 1/2002 | Steiner et al. |
| 2002/0058624 | A1 | 5/2002 | Hanyu et al. |
| 2002/0086829 | A1 | 7/2002 | Gefter |
| 2002/0176846 | A1 | 11/2002 | Hastedt et al. |

OTHER PUBLICATIONS

Munjeri et al., "Hydrogel Beads Based on Amidated Pectins for Colon–Specific Drug Delivery: The Role of Chitosan in Modifying Drug Release," *Journal of controlled Release*, 46:273–278 (1997).

Pilnik et al., "Gelling Agents (Pectins) From Plants For The Food Industry" *Advances in Plant Cell Biochemistry and Biotechnology*, 1:219–270 (1992).

Sriamornsak et al., "Calcium Pectinate Gel Beads for Controlled Release Drug Delivery: 1. Preparation and in Vitro Release Studies," *Int'l Journal of Pharmaceutics*, 160:207–212 (1998).

Sriamornsak, "Preliminary Investigation of Some Polysaccharides as a Carrier for Cell Entrapment," *European Journal of Pharmaceutics and Biopharmceutics*, 46:233–236 (1998).

Thakur et al., "Chemistry and Uses of Pectin—A Review," *Critical Reviews in Food Science and Nutrition*, 37(1):47–73 (1997).

Tibbits et al., "Calcium Binding and Swelling Behaviour of a High Methoxyl Pectin Gel," *Carbohydrate Research*, 310:101–107 (1998).

Wakerly et al., "Studies on Amidated Pectins as Potential Carriers in Colonic Drug Delivery," *J. Pharm. Pharmacol.*, 49:622–625 (1997).

Fishman et al., "Characterization of Pectin, Flash–Extracted from Orange Albedo by Microwave Heating, Under Pressure," *Carbohydrate Research*, 323:126–138 (2000).

Albersheim et al., "Splitting of Pectin Chain Molecules in Neutral Solutions," *Biochemistry and Biophysics*, 90:46–51 (1960).

Anderson, "Human Gene Therapy," *Nature*, 392:25–30 (1998).

Ashford et al., "An Evaluation of Pectin as a Carrier for Drug Targeting to the Colon," *Journal of Controlled Release*, 26:213–220 (1993).

Axelos et al., "Influence of the Substitutents of the Carboxyl Groups and of the Rhamnose Content of the Solution Properties and Flexibility of Pectins," *Int. J. Biol. Macromol.*, 13:77–82 (1991).

Blumenkrantz et al., "New Method for Quantitative Determination of Uronic Acids," *Analytical Biochemistry*, 54:484–489 (1973).

Cohen et al., "A Novel In Situ–Forming Ophthalmic Drug Delivery System from Alginates Undergoing Gelation in the Eye," *Journal of Controlled Release*, 44:201–208 (1997).

Eck et al., "Gene–Based Therapy," *Goodman and Gilman's Pharmacacological Basis of Therapeutics*, McGraw–Hill Publishers, 5:77–101 (1995).

England et al., "Nasal pH Measurement: A Reliable and Repeatable Parameter," *Clinical Otolarygology*, 24:67–68 (1999).

Fisher et al., "Assessment of Accidental Intakes of Uranyl Acetylacetonate (UAA)," *Radiation Protection Dosimetry*, 53(1–4):263–267 (1994).

Gemeiner et al., "Calcium Pectate Gel could be a Better Alternative to Calcium Alginate Gel in Multiple Applications of Immobilized Cells," *Progress in Biotechnology*, 2:76–83 (1996).

Gurny et al., "Ocular Theraphy with Nanoparticulate sYstems for Controlled Drug Delivery," *Journal of Controlled Release*, 2:353–361 (1985).

Ireson et al., "Comparison of nasal pH values in Black and White Individuals with Normal and High Blood Pressure," *Clinical Science*, 100:327–333 (2001).

Jarvis et al., "Structure and Properties of Pectin Gels in Plant Cell Walls," *Plant, Cell and Environment*, 7:153–164 (1984).

Jeong et al., "Biodegradable Block Copolymers as Injectable Drug–Delivery Systems," *Nature*, 388:860–862 (1997).

Jeong et al., "Drug Release from Biodegradable Injectable Thermosensitive Hydrogel of PEG–PLGA–PEG Triblock Copolymers," *Journal of Controlled Release*, 63:155–163 (2000).

Kajiwara et al., "Gels Handbook," *Academic Press*, vol. 1, Chapter 1, Sections 1–2, pp. 3–25 (2001, 1997).

Langer, "Drug Delivery and Targeting," *Nature*, 392(Supp.):5–10 (1998).

Lin et al., "Carbopol/Pluronic Phase Change Solutions for Ophthalmic Drug Delivery," *Journal of Controlled Release*, 69:379–388 (2000).

Lorin et al., "Quantitative Composition of Nasal Secretions in Normal Subjects," *Journal of Laboratory and Clinical Medicine*, 80(2):275–281 (1972).

Maness et al., "Determination of the Degree of Methyl Esterification of Pectins in Small Samples by Selective Reduction of Esterified Galacturonic Acid to Galactose," *Analytical Biochemistry*, 183:346–352 (1990).

Mitterhauszerova et al., "Interaction of Aminopyrine 4–Aminoantipyrine, Nicotine Amide, and P–Aminosalicylate with Pectic Acid," *Pharmacology*, L11:501–507 (1983).

Miyazaki et al., "Oral Mucosal Bioadhesive Tablets of Pectin and HPMC: In Vitro and In Vivo Evaluation," *Int'l Journal of Pharmaceutics*, 204:127–132 (2000).

Moe et al., "Alginates," *Food Polysaccharides and Their Applications*, 9:245–286 (1995).

Nurmukhambetova et al., "Interaction of Cephedrin with Polyelectrolytes," *News of the Nat'l Academy of Sciences of Republic of Kazakhstan, Chemical Series*, 3:58–61 (1995) (English translation provided).

Piculell, "Gelling Carrageenans," *Food Polysaccharides and Their Appplications*, 8:205–239 (1995).

Putney et al., "Improving Protein Therapeutics with Sustained–Release Formulations," *Nature Biotechnology*, 16:153–157 (1998).

Renard et al., "Pectins in Mild Alkaline Conditions: β–elimination and Kinetics of Dementhylation," *Progress in Biotechnology, Pectins and Pectinases*, 14:603–608 (1996).

Rolin, "Pectin," in Industrial Gums, Academic Press, New York, Chapter 10, pp. 258–293 (1993).

Romano et al., "Latest Developments in Gene Transfer Technology: Achievements, Perspectives, and Controversies over Therapeutic Applications," *Stem Cells*, 18:19–39 (2000).

Rozier et al., "Gelrite®: A Novel, Ion–Activated, In–Situ Gelling Polymer for Ophthalmic Vehicles. Effect on Bioavailability of Timolol," *Int 'l Journal of Pharmaceutics*, 57:163–168 (1989).

Rydén et al., "Effect of Polymers and Microspheres on the Nasal Absorption of Insulin in Rats," *Int'l J. Pharm.*, 83:1–10 (1992).

Schipper et al., "Nasal Insulin Delivery with Dimethyl–β–Cyclodextrin as an Absorption Enhancer in Rabbits: Powder More Effective than Liquid Formulations," *Pharm. Res.*, 10(5):682–686 (1993).

Schols et al., "Complex Pectins: Structure Elucidation Using Enzymes," *In Process in Biotechnology 14. Pectins and Pectinases, J. Visser and A.G.J. Voragen (Eds.)*, 3–20 (1996).

Shipunova et al., "Immobilization of Isoniazid on Pectin Compounds," *Institute of Chemical Scienes of Nat'l Academy of Sciences of Republic of Kazakhstan, Alma–ata*, 2:83–88 (1990) (English translation provided).

Somia et al., "Gene Therapy: Trials and Tribulations," *Nature Reviews*, 1:91–99 (2000).

Stjernschantz et al., "Anatomy and Physiology of the Eye, Physiological Aspects of Ocular Drug Therapy," *Biopharmaceutical Aspects of Ocular Drug Delivery*, 1:1–15 (1993).

Vadnere et al., "Thermodynamic Studies on the Gel–sol Transition of some Pluronic Polyols," *International Journal of Pharmaceutics*, 22:207–218 (1984).

Verma et al., "Gene Therapy –Promises, Problems and Prospects," *Nature*, 389:239–242 (1997).

Voragen et al., "Pectins," *Food Polysaccharides and Their Applications*, 10:287–339 (1995).

Voragen et al., "Determination of the Degree of Methylation and Acetylation of Pectings by H.P.L.C., " *Food Hydrocolloids*, 1:65–70 (1986).

Wakerly et al., "Studies on Drug Release from Pectin/Ethycellulose Film–Coated Tablets: A potential Colonic Delivery System," *International Journal of Pharmaceutics*, 153:219–224 (1997).

Yamada, "Contribution of Pectins on Health Care," *Progress in Biotechnology, Pectins and Pectinases*, 14:173–190 (1996).

Zheng et al., "Salt Effects on the Corr–linking Mechanism of Cupric–Induced Sol–Gel Transition in Alginate Solutions," *Carbohydrate Polymers*, 35:215:221 (1998).

Zhubanov et al., "Immobilization of Promedol on Poly–Sugar Supports," *A.B. Bakturov Institute of Chemical Sciences of Nat'l Academy of Sciences of Republic of Kazakhstan, Alma–ata*, (5), 27–31 (English translation provided).

Zhubanov et al., "Pectic Acid and Carboxy Methyl Cellulose as Polymer Hosts for Analgesic Promedol," 6:55–58(English translation provided).

Zhubanov et al., "Application of Carboxy Methyl Cellulose and Pectic Acid to Prolong Clophelin Action," *A.B.Bakturov Institute of Chemical Sciences of Nat'l Academy of Sciences of Republic of Kazakhstan, Alma–ata*, 1:61–65 (1993) (English translation provided).

* cited by examiner

IN-SITU GEL FORMATION OF PECTIN

BACKGROUND

The present invention relates to in-situ gelation of a pectic substance. Specifically, the invention relates to a pectin in-situ gelling formulation for the delivery and sustained release of a physiologically active agent to the body of an animal. More specifically, the pectic substance is derived from Aloe vera L. plant.

Abbreviations Used Herein Include:

CMC, carboxylmethyl cellulose; Da, dalton; DM, degree of methylation; Gal A, galacturonic acid; HEC, hydroxyethyl cellulose; HM, high methoxyl; HPMC, hydroxypropylmethylcellulose; kDa, kilodaltons; LM, low methoxyl; PBS, phosphate buffered saline; PEG-PLGA-PEG, polyethylene glycol-poly(lactic-co-glycolic acid)-polyethylene glycol; PEO-PLLA, poly(ethylene oxide)-poly(L-lactide); PEO-PPO-PEO, poly(ethylene oxide)-poly(propylene oxide)-poly(ethylene oxide).

Pectin is a biodegradable acidic carbohydrate polymer. Pectin is commonly found in plant cell walls. The cell wall of a plant is divided into three layers consisting of the middle lamella, the primary wall and the secondary cell wall. The middle lamella is richest in pectin. The chemistry and biology of pectin have been extensively reviewed (Pilnik and Voragen, *Advances in plant biochemistry and biotechnology* 1, 219–270, 1992; Voragen et al, *In Food polysaccharides and their applications*. pp 287–339. Marcel Dekker, Inc. New York, 1995; Schols and Voragen, *In Progress in Biotechnology* 14. *Pectins and pectinases*, J. Visser and A. G. J. Voragen (eds.). pp. 3–20. Elsevier Science Publishers B. V. Amsterdam, 1996).

Pectin consists of an α-(1→4)-linked polygalacturonic acid backbone intervened by rhamnose residues and modified with neutral sugar side chains and non-sugar components such as methyl and acetyl groups. The extent of rhamnose insertions and other modifications vary depending on plant sources. The Gal A content is generally more than 70% whereas the rhamnose content is typically <2%. Rhamnose residues are α-(1→2)-linked to Gal A residues in the backbone. They cause the formation of a T-shaped kink in the backbone chain, and the increase in rhamnose content leads to more flexible molecules. The neutral sugar side chains are attached to the rhamnose residues in the backbone at the O-3 or O-4 position. The rhamnose residues tend to cluster together on the backbone. Hence, this region with side chains attached is referred to as the "hairy region" while the rest of the backbone is named the "smooth region."

Methylation occurs at carboxyl groups of Gal A residues. The degree of methylation or methyl-esterification ("DM") is defined as the percentage of carboxyl groups (Gal A residues) esterified with methanol. Based on the DM, pectins are divided into two classes, low methoxyl ("LM") pectin with a DM of <50% and a high methoxyl ("HM") pectin with a DM of >50%. Commercial pectins derived from citrus and apples are naturally HM pectins. LM pectins are typically obtained through a chemical de-esterification process. Commercial LM pectins typically have a DM of 20–50%. A completely de-esterified pectin is referred as "pectic acid" or "polygalacturonic acid". Pectic acid in the acid form is insoluble but is soluble in the salt form. The common salt form of pectic acid is either sodium or potassium.

Pectin is most stable at acidic pH levels between approximately 3–4. Below pH 3, methoxyl and acetyl groups and neutral sugar side chains are removed. Under neutral and alkaline conditions, methyl ester groups are saponified and the polygalacturonan backbone breaks through β-elimination-cleavage of glycosidic bonds on the non-reducing ends of methylated Gal A residues. Pectic acids and LM pectins are relatively more resistant to neutral and alkaline conditions since there are only limited numbers of methyl ester groups or none at all.

Current commercial pectins are mainly from citrus and apples. However, besides citrus and apples, pectins can also be isolated from many other plants. All vegetables and fruits that have been examined contain pectins. Pectins from sugar beets, sunflowers, potatoes, and grapefruits are just a few other well known examples.

Both HM and LM pectins form gels. However, these gels form via totally different mechanisms (Voragen et al, *In Food polysaccharides and their applications*. pp 287–339. Marcel Dekker, Inc. New York, 1995). HM pectin forms a gel in the presence of high concentrations of co-solutes (sucrose) at low pH. LM pectin forms a gel in the presence of calcium, thus, it is "calcium-reactive." The calcium-LM pectin gel network is built by formation of what is commonly referred to as an "egg-box" junction zone in which Ca++ causes the cross-linking of two stretches of polygalacturonic acid chains.

HM pectins are generally not reactive with calcium ions and therefore cannot form a calcium gel. However, certain HM pectins have been reported to be calcium sensitive and capable of calcium gel formation. In addition, HM pectins can be made calcium-reactive by a block wise de-esterification process while still having a DM of >50%. See, Christensen et al. U.S. Pat. No. 6,083,540.

Calcium-LM pectin gel formation is influenced by several factors, including DM, ionic strength, pH, and molecular weight (Garnier et al., *Carbohydrate Research* 240, 219–232, 1993; 256, 71–81, 1994). The lower the DM and the higher the molecular weight, the more efficient the gelation. Furthermore, the calcium-LM pectin gelation is more efficient at a neutral pH of ~7.0 than ~3.5. Lastly, the addition of monovalent counter ion (NaCl) enhances the gelation, i.e., less calcium is required for gel formation.

Pectins are typically utilized in the food industry and classified by the FDA as "GRAS" (Generally Regarded As Safe). They have also long been used as colloidal and anti-diarrhea agents. Recently, pectins have been utilized in the areas of medical device and drug delivery (Thakur et al., *Critical Reviews in Food Science & Nutrition* 37, 47–73, 1997). In the case of drug delivery, pectin has found its presence in many experimental formulations for oral drug delivery to the colon because pectin is readily degraded by bacteria present in this region of the intestines. The pectin is either used directly with no gelation involved or a pectin calcium gel is preformed to encapsulate the drug agent before administration. Ashford et al., *J. Controlled Release* 26, 213–220, 1993; 30, 225–232, 1994; Munjeri et al., *J. Controlled Release* 46, 273–278, 1997; Wakerly et al., *J. Pharmacy & Pharmacology* 49, 622–625, 1997; *International Journal of Pharmaceutics* 153,219–224,1997; Miyazaki et al., *International Journal of Pharmaceutics* 204, 127–132, 2000. Prior to the present invention, there appears to be no attempt made to examine the in-situ gelling ability of pectins.

Aloe pectin isolated from Aloe vera plant as described in U.S. Pat. No. 5,929,051, the entire content of which is incorporated herein by reference. It is naturally a LM pectin and capable of calcium gelation. In addition, it possesses several unique chemical properties that are particularly related to gelation, including a high molecular weight (>1× $10^6$ Da), a high Gal A content (as high as >90%), and a low DM (<10%).

Current commercial pectins typically have a size of 7–14×$10^4$ Da and Gal A content of ~75% (Voragen et al, *In Food polysaccharides and their applications*. pp 287–339. Marcel Dekker, Inc. New York, 1995). These pectins have a rhamnose content of <2%. Commercial LM pectins and other natural LM pectins have a DM of >20%. A DM below 10% makes Aloe pectin nearly a pectic acid. A pectin with such a low DM, a high molecular weight, and a high Gal A content has not been described previously. Aloe pectin is an off white powder as the finished product, whereas all current commercial and experimental pectins are yellow to tan powders.

Drug delivery has been a subject of intense studies over recent years. The goal is to achieve sustained (or slow) and/or controlled drug release and thereby improve efficacy, safety, and/or patient comfort. A sustained and/or controlled release of the drug agents is achieved by the retardation of drug diffusion by and/or gradual disintegration of the polymer matrix following application.

In-situ gelation is a process of gel formation at the site of application after the composition or formulation has been applied to the site. In the field of human and animal medicine, the sites of application refers to various injection sites, topical application sites, surgical sites, and others where the agents are brought into contact with tissues or body fluids. As a drug delivery agent, the in-situ gel has an advantage related to the gel or polymer network being formed in-situ providing sustained release of the drug agent. At the same time, it permits the drug to be delivered in a liquid form.

Polymers capable of in-situ gelation have been described. They include Poloxamer, Pluronics (Vadnere et al., *Int. J. Pharm.*, 22, 207–218, 1984), various copolymers such as PEO-PLLA and PEG-PLGA-PEG (Jeong et al., *Nature* 388, 860–862, 1997; Jeong et al., *J. Controlled Release* 63, 155–163, 2000), cellulose acetophalate latex (Gurny et al. *J. Controlled Release* 353–361, 1985), Gelrite (Rozier et al., *Int. J. Pham.* 57, 163–168, 1989), Carbopol, and Matrigel. The gel formation is induced by temperature change (Poloxamer, Pluronics, PEO-PLLA diblock copolymer, PEG-PLGA-PEG triblock copolymer, and Matrigel), pH change (cellulose acetophalate latex and Carbopol), or reaction with mono- or di-valent cations (Gelrite). However, most of them require a high polymer concentration for in-situ gel formation (>20%) (Poloxamer, PEO-PLLA diblock copoly, PEG-PLGA-PEG triblock copolymer, cellulose and acetophalate latex). The thermally gelling polymers (Poloxamer, Pluronics, PEO-PLLA diblock copolymer, PEG-PLGA-PEG triblock copolymer, and Matrigel) also have the disadvantage of gelling before administration due to temperature change during packaging or storage. Unfortunately some of these polymers are not biodegradable such as Poloxamer or require manipulation of the temperature before administration (PEO-PLLA diblock copolymer) or during formulation (Pluronics and Gelrite). An ophthalmic in-situ gelling drug delivery formulation consisting of a mixture of Carbopol and Pluronic was found to be more effective than formulations consisting of either one. However, Pluronic is used at 14% (Lin and Sung, *Journal of Controlled Release* 69, 379–388, 2000). Such polymers are therefore not well suited for medical applications in humans and animals. Furthermore, many of these polymers form only a hydrogel which is a viscous but still flowing solution (e.g., Poloxamer and Pluronics).

The in-situ gelation compositions using ionic polysaccharides have been disclosed in U.S. Pat. No. 5,958,443, which consist of a drug, a polymer and a gel forming ionic polysaccharide which consist of two components, an ionic polysaccharide and a cross-linking ion capable of cross-linking the former. The in-situ gel formation is induced by the application of the cross-linking ions.

Thus, a great need exists for a simpler and more efficient in-situ gelling composition that employs only a low polymer concentration for the purposes of drug delivery.

SUMMARY OF THE INVENTION

One embodiment of the present invention pertains to using a pectic substance to provide a biodegradable in-situ gelling composition for animal and human use. The composition transforms from a liquid into a gel following administration to the target site. Preferably the pectic substance is Aloe pectin.

One object of the present invention is to provide a composition for controlled, or sustained, release of a physiologically active agent in the body of an animal.

Another object of the present invention is to provide for a transparent polymer solution wherein no dramatic increase in gel cloudiness is created beyond certain concentration ranges. Preferably the composition is capable of creating an in-situ gel at low concentrations.

Another object of the present invention is to provide for a transparent polymer solution wherein a thickener is added. Preferably the composition is capable of creating an in-situ gel at low concentrations.

A further object of the present invention is to provide for a composition that is capable of creating an in-situ gel at low concentrations once delivered in the liquid form.

Another object of the present invention is to provide for a composition for drug delivery. In the case of drug delivery, for example, a therapeutic or diagnostic agent is incorporated into the formulation or composition. These agents can be small molecules as well as large ones such as proteins. Preferably the composition is capable of forming an in-situ gel at low concentrations.

These and other objects of the present invention are provided by the described embodiments of the present invention. The foregoing discussion has outlined some of the more pertinent features of the present invention. These should be construed to be merely illustrative of some of the more prominent features and applications of the invention. Accordingly, a fuller understanding of the invention maybe had by referring to the following Detailed Description.

BRIEF DESCRIPTION OF THE DRAWINGS

For a more complete understanding of the preferred embodiment of the present invention, reference is made to the following detailed description taken in conjunction with the accompanying drawings, wherein like numerals refer to like elements, wherein.

DETAILED DESCRIPTION

Figure 1:
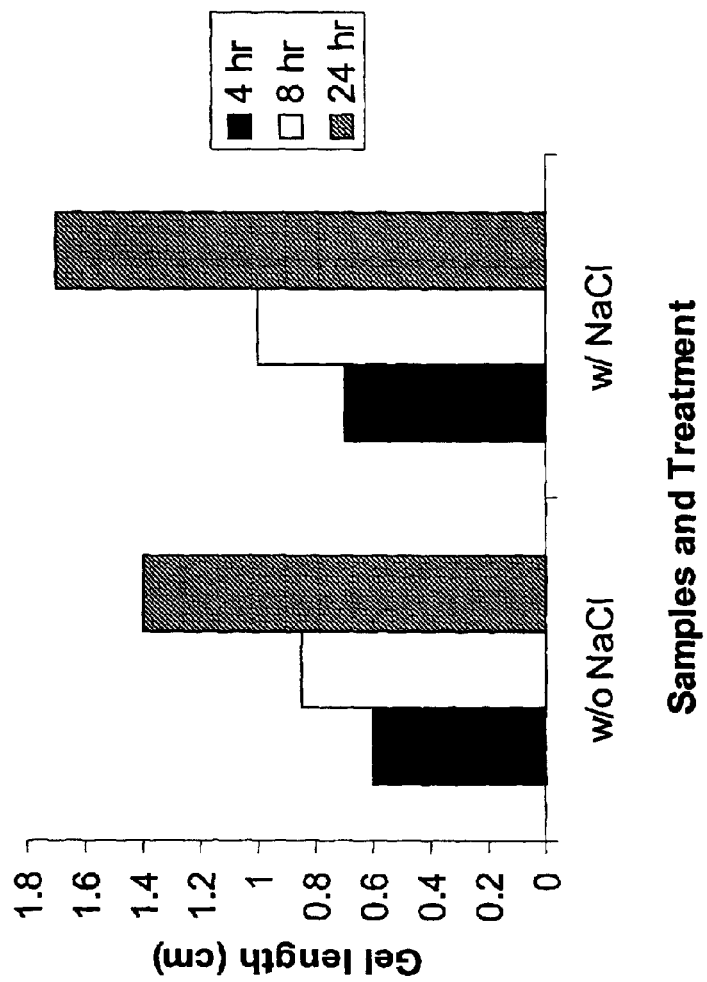
FIG. 1 is a bar graph representing the relationship of NaCl to the calcium gelation of Aloe pectin.

Thus, the general term "pectic substance," as used in this invention, includes pectin, low and high methoxyl pectin, de-esterified pectin, pectin calcium gel, Aloe pectin sodium gel, pectic acid, pectate, pectinic acid, pectinate, protopectin, and pectin-rich substances, such as Aloe vera inner gel cell wall fiber, individually, collectively, or in combination thereof. As discussed above, pectin is a group designation for those complex colloidal carbohydrate derivatives which occur in, or are prepared from, plants and contain a large proportion of anhydrogalacturonic acid units which are thought to exist in a chain-like combination. The carboxyl groups may be partially esterified by methyl groups and partially or completely neutralized by one or more bases. Thus, "deesterified" usually means that one or more methyl ester groups have been removed from the pectin molecules. "Pectic acids" is the group designation applied to pectic substances mostly composed of colloidal polygalacturonic acids and essentially free from methyl ester groups. The totally de-esterified pectin is pectic acid or polygalacturonic acid. "Pectates" are either normal or acid salts of pectic acids. "Pectinic acids" are the colloidal polygalacturonic acids containing more than a negligible proportion of methyl ester groups. "Pectinates" are either normal or acid salts of pectinic acids. "Protopectin" is applied to the water-insoluble parent pectin which occurs in plants and which upon restricted hydrolysis yields pectins, pectinic acids, and others. The water-insoluble pectin may be associated with the cellulose present in the plant, such as the Aloe vera inner gel or rind cell wall fiber.

Aloe Pectin

Aloe vera leaves consist of two parts, an outer green rind and a clear inner gel which is also referred to as pulp. Aloe pectin is extracted from the inner gel or outer rind cell wall fibers. Use of a chelating agent at a slight alkaline pH is found to be the most efficient extraction method. Aloe pectin is unique as compared to previously described pectins. It has a high rhamnose content of >4% in the purified pectin preparation which is at least 2 times higher than described in other pectins such as citrus, apple, sugar beet, and sunflower. Rhamnose is a key sugar in the pectin backbone whose content affects the flexibility of the molecule. Aloe pectin also possesses a rare sugar, 3-OMe-rhamnose which has not been described in any other pectins. Aloe pectin is naturally LM, having a DM generally <30% and can be as low as <10%. The Gal A content of Aloe pectin is >70% and can be as high as >90%. Aloe pectin is capable of gel formation in the presence of calcium. A monovalent cation, such as sodium, potassium and lithium accelerates the formation of gel.

Aloe pectin can be distinguished from other pectins by one or more of the following characteristics:

1) A high molecular weight (>$1\times10^6$ Da) and a high intrinsic viscosity (>550 ml/g);
2) A high rhanmose content (>4%);
3) A high galacturonic acid content (>90%);
4) Containing 3-OMe-rhamnose;
5) Being naturally LM with a DM as low as <10%;
6) Capable of calcium gel formation;
7) Capable of monovalent cation-based gel formation at low temperature (4° C.).

We found that by injecting into a body or by topically applying to wound surfaces as a route of administration, a non-gelled liquid pectin can form a gel in-situ at the site of administration. The in-situ gel is firm and non-flowing just like the calcium gel formed in vitro, which is distinct from the hydrogel, a viscous but still flowing solution. The in-situ gelation of Aloe pectin was found to be particularly efficient such that the minimal Aloe pectin concentration needed for forming a firm solid in-situ gel is as low as 2.5 mg/ml or 0.25% (w/v) and can be even lower if a thickener is added.

The gel compositions can be made isotonic or iso-osmotic and adjusted to the pH of mammalian body fluids, such as lacrimal tears. The pH and osmotic pressure of such bodily fluids are 7.4 and 29 mOsm/kg, respectively. It is advantageous to deliver a pharmacologically active medicament to an area of the mammalian body requiring pharmacological treatment under desired pH and osmotic pressure conditions which, for instance, match those of bodily fluids. Optionally, the pharmaceutical compositions of the invention can be provided in a sterile condition.

Although not wanting to be bound by any theory, it is believed that the pectin in-situ gelation is primarily mediated by the calcium ions in the body fluids. Blood has a calcium concentration of 8.5–10.3 mEq/dl. The calcium gelation of pectins is enhanced in the presence of NaCl which is also a normal component of the body fluids. There are 134 mEq/L NaCl in the blood.

The in-situ gel also forms in the presence of various agents, including small organic compounds, proteins, nucleic acid, live cells, and other polymers following subcutaneous injection, demonstrating the capability of the pectin for delivering a wide range of agents in an encapsulated or entrapped form. When a poorly soluble compound such as silvadene was incorporated, the in-situ gel still formed. Once delivered, the pectin in-situ gel clearly exerted a slow release effect. This was demonstrated under in vitro as well as in vivo conditions with a small organic model compound (fast green). In addition, when bFGF is delivered with the pectin in-situ gel, a significantly increased cell proliferation surrounding the gel was observed.

Aloe pectin is more efficient than current commercial pectins including LM pectins, and polygalacturonic acid, and amidated LM pectins for in-situ gelation. A well-formed in-situ gel was only obtained with commercial polygalacturonic acid or LM pectin at a concentration 10 times higher than that for Aloe pectin. Current commercial LM pectins and polygalacturonic acids have a lower Gal A content (~75%), a much lower molecular weight (7–14×$10^4$ Da), and a DM of 20–50%. There are other polymers that can form a calcium gel. One example is alginate. However, alginate was not capable of forming a well defined in-situ gel at concentrations tested. Alginate is a polysaccharide block copolymer consisting of guluronic acid (G) and manuronic acid (M) (Moe et al., In Food polysaccharides and their applications. pp 287–339. Marcel Dekker, Inc. New York, 1995). These two residues in alginates exist as G-block, M-block, or alternating MG-block. Only the G-block is responsible for calcium gelation. The total G content varies widely dependent on the sources; the highest G content is ~70%. In addition, the alginate calcium gelation is inhibited by the presence of NaCl, which exists in the physiological fluids.

Several other polymers have also been shown to be capable of in-situ gelation. However, most of them require a high polymer concentration for in-situ gel formation (>20%) (Poloxamer, PEO-PLLA diblock copoly, PEG-PLGA-PEG triblock copolymer, cellulose and acetophalate latex). Some of these polymers are not biodegradable, such as Poloxamer, or require manipulation of the temperature before administration (PEO-PLLA diblock copolymer) or during formulation (Pluronics and Gelrite). The thermally gelling polymers (Poloxamer, Pluronics, PEO-PLLA diblock copolymer, PEG-PLGA-PEG triblock copolymer, and Matrigel) also have the disadvantage of gelling before administration due to ambient temperature changes during packaging or storage. Furthermore, many of these polymers form only a hydrogel, a viscous but still flowing solution (e.g., Poloxamer and Pluronics). In addition, some polymer formulations require two different polymers or the application of a second component for gelation to occur.

Pectin, especially the Aloe pectin, is advantageous over these polymers or compositions in that the polymer concentration required to achieve the in-situ gelation is very low ($\geq 0.25\%$, w/v) and can be even lower if a thickener is added. The preparation does not require temperature or pH adjustment, or application of a second component for the in-situ gelation to occur. The gel is transparent, and there is no dramatic increase in gel cloudiness beyond certain concentration ranges as with PEG-PLGA-PEG triblock copolymer and Pluronics.

The advancement of biotechnology is generating more and more protein-based therapeutics. Proteins are inherently unstable. Proper formulation and delivery are critical to their in vivo functions (Langer, *Nature* 392, 5–10, 1998; Putney and Burke, *Nature Biotechnology* 16, 153–157, 1998). The pectin in-situ gel is particularly suited for protein delivery because of its mild gelling conditions. Many protein agents are also intended to be delivered locally in a sustained manner, e.g., growth factors for wound healing and angiogenic factors for therapeutic angiogenesis. This can also be achieved with pectin in-situ gel. When bFGF was delivered with the Aloe pectin in-situ gel, a significantly increased cell proliferation surrounding the gel was observed.

As used herein, the term "physiologically active agent" refers to an agent that can exert a physiological response in the body of an animal. The physiologically active agent includes, for example, a pharmacologically active substance; a small molecule, such as an inorganic compound, an organic compound and its salt thereof; a diagnostic agent; a therapeutic agent; a nucleic acid; a peptide; a polymer; a small protein; a large protein; and a live cell. A pharmacologically active substance includes a substance that illicits immune response, such as a vaccine. Examples of therapeutic agents include anti-bacterial substances, antimicrobial agents, antiparasitic agents, antibiotics, antihistamines, decongestants, antimetabolites, antiglaucoma agents, anticancer agents, antiviral agents, anti-fungal agents, anti-inflammatory agents, anti-diabetic agents, anesthetic agents, anti-depressant agents, analgesics, anti-coagulants, opthalmic agents, angiogenic factors, immunosuppressants, and anti-allergic agents. Based on the weight of the final composition or formulation, the physiologically active agent can vary from about 0.01% to about over 90%. The amount of the physiologically active agent used would depend on the type, form, and nature of the physiologically active agent.

The range of the pectic substance can vary from about 0.01% to about 40%, based on the total weight of the composition, preferably from about 0.1% to about 20%, and more preferably from about 0.25% to about 2%. The amount of the pectic substance used would depend on the type, form, and nature of the physiologically active agent. Optionally, a carrier or excipient may be used.

A carrier used for this invention includes any pharmaceutically acceptable carrier, such as water; saline; a buffered aqueous solution; emulsion, such as oil/water emulsion; adjuvant; a wetting agent; tablet; and capsule. Based on the weight of the final composition or formulation, the carrier can vary from about 0% to about 90%. The amount of carrier present would depend on the physiologically active agent and the manner by which the formulation or composition is to be delivered.

Representative buffering agents include alkali or alkali earth carbonate, chloride, sulfate, phosphate, bicarbonate, citrate, borate, acetate, and succinate. Representative preservatives include sodium bisulfite, sodium thiosulfate, ascorbate, benzalkonium chloride, chlorobutanol, thimerosal, phenylmercuric borate, paraben, benzylalcohol, and phenylethanol.

Thus, one embodiment of the current invention is to provide a composition for the sustained delivery of a physiologically active compound, and the composition contains a pectin and a physiologically active compound with or without a pharmaceutically acceptable thickener. Preferably, the composition changes from a liquid to a gel upon administration of the composition to the body of an animal, and thus the release of the physiologically active compound is sustained or controlled.

A biodegradable thickener such as CMC, HPMC, sodium alginate, collagen, gelatin, and hyaluronic acid may be added to the formulation. Addition of such a thickener does not influence the gelling efficiency as described below, but provides an advantage of enhancing the density of the gel matrix and the in-situ gel formation at lower pectin concentrations. In addition, polymers that are responsive to changes in pH, ionic strength, and temperature may also be used as long as they are synergistic with the pectin gelation. Furthermore, a blend of different pectins may be used with or without a thickener. Other thickeners include Carbopol, Gelrite, chitosan, and xyloglucan. Based on the weight of the final composition or formulation, the thickener can vary from about 0% to about 90%. The amount of biodegradable thickener used would depend on the physiologically active agent and the manner of which the composition or formulation is used.

Still another embodiment of the current invention is to provide a composition consisting of a pectin with or without a pharmaceutically acceptable thickener for use as a medical device.

Preferably, the pectic substance is a calcium reactive. More preferably, the pectic substance is a LM pectin or polygalacturonic acid. Still more preferably, the pectic substance is Aloe pectin.

The calcium reactivity can be determined by methods including gel formation, change in viscosity, and potentiometry.

The term "gel formation" refers to an increase in viscosity of a solution triggered by a change in the physical or chemical condition. The gel formed can be a viscous liquid, a solid, or in any state in between. Gels in various states may be obtained by adjusting the polymer concentration or other factors. A gel in a particular state can be most suited for certain applications.

A pectin in-situ gelling compositions containing a therapeutic or diagnostic agent(s) may be administered or delivered to the animal by various means. For example, it may be applied topically to the eyes, mucosal surfaces, or wounds. It may also be delivered parenterally, such as subcutaneously, intramuscularly, or via intraperitoneal injection. It may also be injected into an organ, a joint cavity, or a tumor.

Pectin can be extracted from many different plant sources. Besides citrus and apples, for example, pectin has also been obtained from potatoes, grape fruits, sugar beets, and sunflower heads. Pectin may be modified. For example, an amidated pectin is produced by treatment with ammonia. It is conceivable that an Aloe-pectin-like pectin may be present in a different plant species or a pectin from a different plant source may be produced, re-processed, and/or modified in a way to enhance the in-situ gelling ability based on the principles disclosed herein. Furthermore, although an LM pectin with a DM >50% is preferred for use in the present invention because of its calcium reactivity, certain HM pectins are also known to be calcium-sensitive and capable of forming calcium gel, and may therefore be used for in-situ gelling (Tibbits et al., *Carbohydrate research* 310, 101–107, 1998). In addition, a block wise de-esterified HM pectin that still has a DM of >50%, but is rendered calcium sensitive by the block wise de-esterification, may also be used. See, Christensen et al. U.S. Pat. No. 6,083,540.

Thus, it should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims.

EXAMPLE 1

In-situ Gelation of Aloe Pectin

Extraction of Aloe pectin

Aloe pectin was extracted from cell wall fibers prepared from either pulp or rind of Aloe vera leaves. The general methods of extracting pectins have been reported. See, Voragen et al, *In Food polysaccharides and their applications*. pp 287–339. Marcel Dekker, Inc. New York, 1995. See also, U.S. Pat. No. 5,929,051, the entire content of which is hereby specifically incorporated by reference. The extraction of Aloe pectin was achieved with a chelating agent such as EDTA or under other conditions including hot water, hot diluted acid (HCl, pH 1.5–3), and cold diluted base (NaOH and $Na_2CO_3$; pH 10).

Following the extraction, the remaining fibers were removed by coarse and fine filtrations. The pectin was precipitated with ethanol. The pectin precipitates were further rinsed with ethanol solutions before being dried.

Aloe pectins obtained in this manner from either pulp or rind cell wall fibers were characterized with a molecular weight ($\geq 1 \times 10^5$ Da), a low DM (<50%), and a Gal A content (>80%). Preferably, the molecular weight was $>1 \times 10^6$ Da, the DM was <10%, and the Gal A content was >90%.

The molecular weight was determined by HPLC-based size exclusion chromatography with pullulan as the standard. DM was determined by a selective reduction method (Maness et al., *Analytical Biochemistry* 185, 346–352, 1990) and a HPLC-based method (Voragen et al., *Food Hydrocolloids*, 1, 65–70, 1986). Gal A content was determined by m-hydroxyldiphenyl method (Blumenkrantz, N. and Asboe-Hansen, G. *Analytical Biochemistry* 54, 484–489, 1973). The content of each of these three references is hereby incorporated by reference.

In-situ gelation of Aloe pectin

Aloe pectin was first dissolved in sterile deionized water and then mixed with equal volume of 2×physiological saline (0.3 M NaCl). Aloe pectin could not be readily dissolved in salt solution. However, once dissolved in water, the pectin can be mixed with the salt solution to achieve the physiological ionic strength. The pectin solution in physiological saline obtained in this manner remained clear. The pectin solutions were free-flowing at room temperature and had a pH of 5.0–6.0 depending on the polymer concentrations. No adjustment of temperature or pH was performed unless otherwise indicated. The preparation was injected subcutaneously into lower abdominal regions of Swiss Webster mice (0.05 or 0.1 ml per site) in accordance with the animal use protocols. Mice were sacrificed at various times following injection and the gel formation was examined.

The swelling of the skin at the injection site did not disappear over time as in the case of the saline control. When the skin over the injection site was surgically incised, a piece of gel shaped like a ball or an oval was observed. The gel was clear, transparent, and firm. It could be readily separated from surrounding tissues. The gel was surgically excised along with skin, fixed in formalin, sectioned, stained with H&E, and examined under the microscope. The gel was only lightly stained but was clearly visible and surrounded by the dermal tissues. The same in-situ gelation was also observed in rats. The swelling at the injection site was not as evident in rats as in mice due to the thicker skin and hair coat. However, when skin at the injection site was surgically incised, the same in-situ gel was observed. With rats, one ml of Aloe pectin solution could be injected subcutaneously at the lower abdominal region and correspondingly much larger gel pieces were obtained.

The gel formation is pectin concentration-dependent. At a concentration of $\geq 0.25\%$ (w/v), a solid firm gel was obtained. No gel formation was observed at $\leq 0.1\%$ (w/v). At concentrations between 0.1% and 0.25%, a soft gel was obtained.

The in-situ gel also formed when the pH of the Aloe pectin solution was adjusted to ~7.2 with dilute sodium hydroxide.

The in-situ gelling ability is dependent on the molecular weight of Aloe pectin. When an Aloe pectin with a much reduced molecular weight ($\sim 3 \times 10^4$ Da) but the same DM and Gal A content was used, no in-situ gelation was observed when tested at 0.5% (w/v).

The in-situ gel also formed following injection through intraperitoneal and intramuscular routes although the gel formed did not appear to have as uniform a shape as that formed following subcutaneous injection.

EXAMPLE 2

In-situ Gelation Following Topical Application to Wound Surface

Aloe pectin preparation (0.5%, w/v) in physiological saline was directly applied to fresh full-thickness excisional skin wounds on mice or rats. A 0.5% (w/v) CMC preparation in physiological saline and a commercial hydrogel wound dressing were used as a control. The wounds were made with a biopsy punch in accordance with animal use protocols. After 4 hrs, rats were sacrificed and wounds surgically removed. Wounds were fixed in formalin, sectioned, and stained with H&E. A layer of gel was clearly formed on the surface of wounds with the Aloe pectin preparation but not with CMC or the commercial hydrogel wound dressing.

EXAMPLE 3

Pectin In-Situ Gelation Mediated by Calcium Ions

Body fluids such as blood and lacrimal fluid contain calcium ions (8.5–10.3 mEq/dl in blood). Since Aloe pectin forms calcium gel, the role of calcium in the in-situ gelation of Aloe pectin was examined using an in vitro gelling system with animal serum that mimics the in-situ gel formation. This in vitro assay is described as a gel frontal migration assay in which animal serum was placed at the bottom of a glass tube and the Aloe pectin solution is layered on top of the serum (the pectin solution may be placed at the bottom of the tube dependent on the density of the test solution in relation to the pectin solution). The gel formed in the pectin phase can be distinguished from the pectin solution by its increased turbidity when examined under a light source. Also, tilting the tube does not move the interface if a gel is formed.

Tissue culture grade normal calf serum was used. Two ml of serum was placed at the bottom of a glass tube (0.8×11 cm) and 1 ml pectin solution (0.5–0.75%, w/v) was placed on top of it. The gel formation was immediate at the contact line or interphase and the gel phase or gel front gradually extended upward in the pectin solution over time. However, if the serum was first dialyzed against saline or EDTA (a chelator for divalent cations) or EGTA (a specific chelator for calcium) was added to the serum to a final concentration of 10 mM, no gel formation was observed. This indicates that the calcium is responsible for the pectin in-situ gelation.

The pectin in-situ gelation also occurred with heparinized whole mouse blood or plasma isolated therefrom.

EXAMPLE 4

Pectin In-Situ Gelation with Other Body Fluids

Besides serum or blood, there are many other types of body fluids such as tear fluid. To determine if the pectin in-situ gelation also occurred with other body fluids, the gel frontal migration assay described in Example 3 was used along with Aloe pectin (0.25% in saline).

The gel formation occurred with the peritoneal fluid. In this case, the ascites from mice injected with hybridoma for monoclonal antibody production was used as peritoneal fluid.

The gel formation also occurred with simulated body fluids. They are:

1) Tear fluid (0.68 g NaCl, 0.22 g $NaHCO_3$, 0.008 g $CaCl_2.2H_2O$, and 0.14 g KCl per 100 ml. (See, Stjernschantz and Asitin, in Edman, P. (ed.), "Biopharmaceutics of Ocular Drug Delivery," CRC Press, Boca Raton, pp. 1–15, 1993. Alternatively, 0.268 g bovine serum albumin, 0.268 glysozyrne, 0.134 g globulin, 0.008 g $CaCl_2.2H_2O$, 0.650 g D-glucose, and 0.658 g NaCl per 100 ml. See, Cohen et al., *Journal of Controlled Release* 44, 201–208, 1997);

2) Lung fluid (0.01 g $MgCl_2.6H_2O$, 0.61 g NaCl, 0.03 g KCl, 0.027 g $Na_2HPO_4.7H_2O$, 0.007 g $Na_2SO_4$, 0.018 g $CaCl_2.2H_2O$, 0.095 g $NaHC_2.3H_2O$, 0.26 g $NaHCO_3$, and 0.01 g $Na_3H\ C_6O_7.2H_2O$ per 100 ml. See, Fisher and Briant, *Radiation Protection Dosimetry*, 53, 263–267, 1994); and 3) Nasal secretion (0.867 g NaCl, 0.44 g $Na_2HPO_4$, 0.108 g $NaH_2PO_4$, 0.058 g $CaCl_2.2H_2O$, 0.31 g KCl 0.636 g albumin per 100 ml. See, Lorin et al., *Journal of Laboratory Clinical Medicine*, 2, 275–267, 1994).

EXAMPLE 5

NaCl Enhances Pectin Calcium Gelation

Body fluids such as blood and lacrimal fluids also contain sodium ions (135–146 mEq/L in blood). Pharmacological preparations for topical or parenteral use are prepared in a buffered or non-buffered physiological saline (0.15 M NaCl) or isotonic solution. NaCl has been shown to enhance the calcium gelation of LM pectins. To determine if the same effect occurs with Aloe pectin, the same gel frontal migration assay was used. Aloe pectin (0.5%, w/v) solutions prepared in 0.15 M NaCl (2 ml) were placed at the bottom of the tube and a 100 mM $CaCl_2$ solution (0.05 ml) was placed on top of the pectin solution. The gel formed extending downward in the pectin solution over time. The migration of the gel front was measured at 18 hrs following the addition of $CaCl_2$. The results showed that the gel front migrated faster in the presence of NaCl, i.e., the calcium gelation of Aloe pectin was enhanced by the presence of NaCl (FIG. 1). The effect of NaCl was also dose-dependent; the gel formation rate was faster in 0.15 M NaCl than in 0.05 M NaCl.

These observations are consistent with previous findings with other LM pectins (Gamier et al., *Carbohydrate Research* 240, 219–232, 1993; 256, 71–81, 1994). FIG. 1 is a bar graph representing the relationship of NaCl to the calcium gelation of Aloe pectin.

EXAMPLE 6

Pectin In-Situ Gelation is Faster at Low Pectin Concentrations

Figure 2:
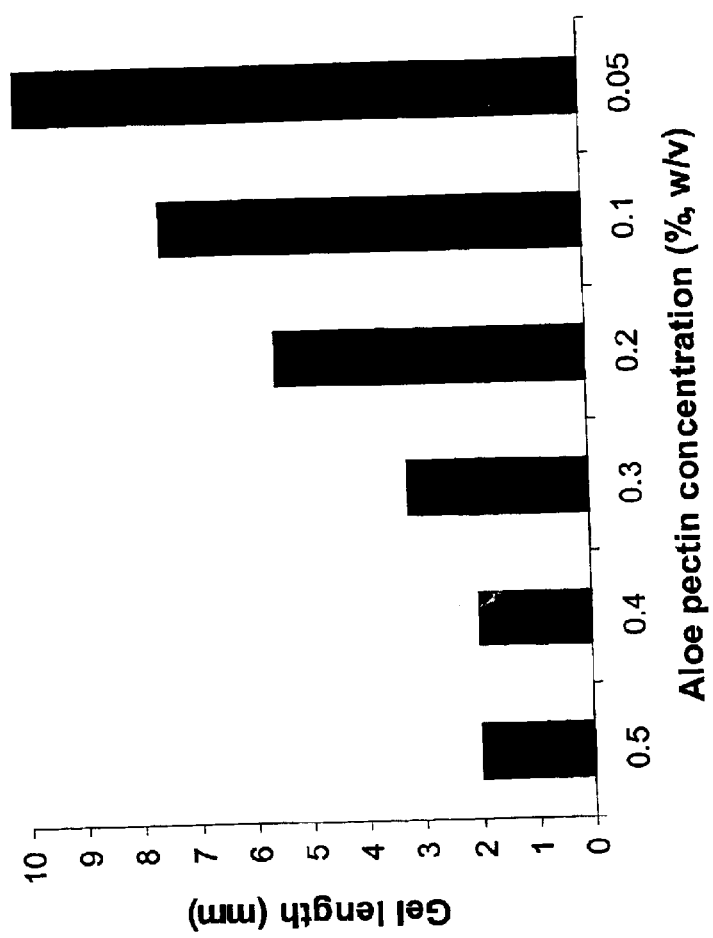
FIG. 2 shows the Aloe pectin in-situ gelation at various Aloe pectin concentrations with normal animal serum.

The gel frontal migration assay described above was used. Aloe pectin at various concentrations in saline (1 ml) was applied onto the normal calf serum (2 ml). After 18 hrs at room temperature, the length of gels formed was measured. The initial gelation at the contact phase is immediate regardless of the pectin concentration. However, the rate at which the gel length grew over time differed at different pectin concentrations. It was found that the lower the pectin concentration, the faster the gelation; the length of the gel formed at 0.05% (w/v) was nearly 5 times longer than that at 0.5% (w/v) (FIG. 2). The gel formed at low concentrations (<0.2%, w/v) was much softer and could be broken by strong agitation.

The same observation was also made when a calcium chloride solution was used to replace the serum. This indicates that the rate of pectin calcium gelation is increased at lower pectin concentrations.

EXAMPLE 7

Addition of Other Polymers or Thickeners Enhances the Pectin

In-Situ Gel Formation

Figure 3:
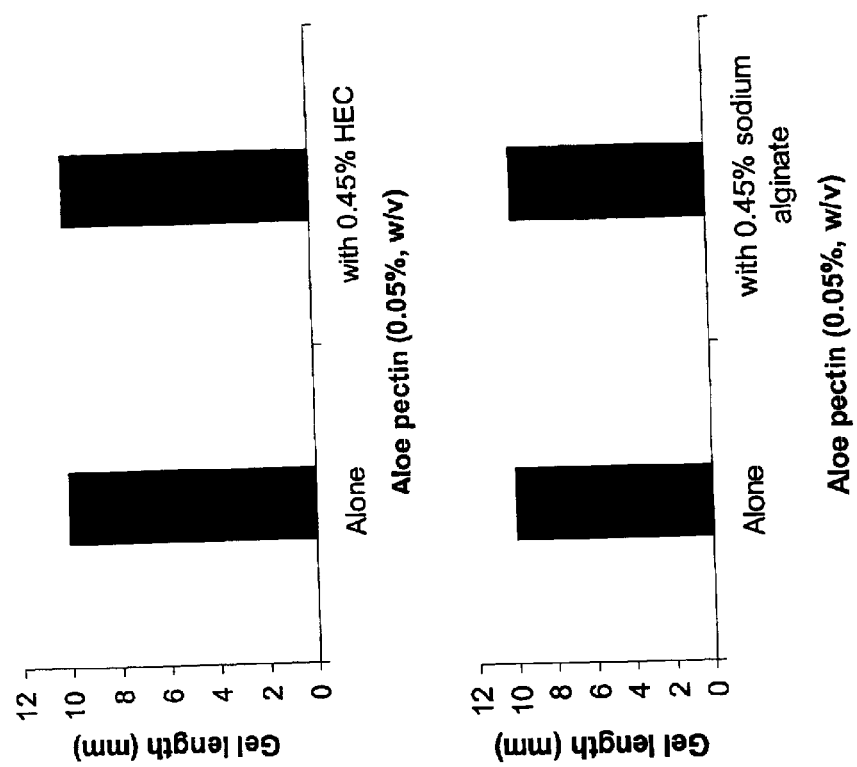
FIG. 3 shows the Aloe pectin in-situ gelation in the presence of a thickener (HEC or alginate) with normal animal serum.

The gel frontal migration assay described above was used. Polymers such as HEC (0.45%, w/v), CMC (0.45%, w/v), or sodium alginate (0.45%, w/v) were mixed with Aloe pectin (0.05%, w/v). Sodium alginate, although capable forming calcium gel with $CaCl_2$ solutions under in vitro conditions, did not form an in-situ gel with the serum. One ml of the polymer solution was applied onto 2 ml normal calf serum. The length of gels formed was measured 18 hrs later. The results showed that addition of other polymers did not influence the rate of the pectin in-situ gelation (FIG. 3). The same result was also obtained when the polymer was mixed with Aloe pectin at a different ratio (0.4% vs 0.1%).

In the in vivo mouse model, a mixture of Aloe pectin (0.375%, w/v) and CMC (0.375%, w/v) in saline formed an in-situ gel following subcutaneous injection. In addition, the addition of a thickener (sodium alginate or HEC at 0.4% or 0.3%, w/v) made it possible to obtain a better formed in-situ gel at low Aloe pectin concentrations (0.1% or 0.2%, w/v) at which the in-situ gels were either soft or not formed with Aloe pectin alone (Example 1).

EXAMPLE 8

Comparison with Other Pectins and Alginates

LM pectins that are capable of calcium gelation were used in the experiments. They included a LM pectin from citrus with a DM of 28% and a polygalacturonic acid prepared from apple pectin (DM=0), both of which were obtained from Sigma Chemical Co., and an amidated pectin with a DM of 28–34% and a DA (degree of amidation) of 16–22%. Before use, they were dissolved in de-ionized water, filtered, ethanol precipitated, and dried.

The in-situ gelation experiment in mouse by subcutaneous route was performed as described in Example 1. Four injection sites on two mice were used for each sample. The results showed that following subcutaneous injection, no in-situ gel formation was observed with any of them at a concentration of 1.0 or 1.65% (w/v). Only smear-like gel substances were observed. However, when tested at a higher concentration (3.0 or 3.3%, w/v), well formed gels were obtained with both polygalacturonic acid and amidated LM pectin.

Similarly, the low molecular weight of Aloe pectin described in Example 1 also gelled in situ at a high concentration (2.5%, w/v).

An HM citrus pectin with a DM of 64% was also tested. It was prepared in the same way as that for the LM pectins. No gel formation was observed for the HM pectin at a concentration of 3% (w/v). The injection site was wet and watery and no solid gel pieces were observed.

Alginates were also tested, including Keltone HVCR and the high G alginate Manugel DMB (G content, 60–70%) at a concentration of 0.5%. Only a smear-like gel substance was observed when examined 4 hrs post subcutaneous injection, indicating that most of the materials had diffused away without gelling. The alginates also did not form a gel with the normal animal serum in the in vitro in-situ gelation assay as described above (Example 7).

These results together showed that the LM pectin, polygalacturonic acid, amidated LM pectin, and alginate are much less efficient than Aloe pectin for in-situ gelation, under the same concentrations.

EXAMPLE 9

Delivery of Physiologically Active Agents by Pectin In-Situ Gel

For the in-situ gelation to be used for drug delivery, the phenomena must occur in the presence of the drug or diagnostic agents. Thus, various compounds or agents were mixed with Aloe pectin in physiological saline with a final pectin concentration of 0.5% (w/v). These compounds or agents were a small organic compound (fast green, 808 Da, 10 mg/ml), a small protein (bFGF, 17 kDa, 10 µg/ml), a medium-sized protein (bovine serum albumin, 66 kDa, 10 mg/ml), a large-size protein (type I bovine collagen, 2 mg/ml), a nucleic acid (Lamda DNA Hind III fragments, 200 µg/ml), a carbohydrate polymer (CMC, 0.5%, w/v), and Raw 264.7 cells (a mouse macrophage line, $1\times10^8$/ml). The mixtures were injected subcutaneously into mice. Gel formation was then examined 4 hrs after injection. The results showed that the gel formation occurred in the presence of all the agents tested as the Aloe pectin alone control. The concentrations of the drug agents used were those tested and were not the maximum concentration possible.

Furthermore, by gel frontal migration assay, the in-situ gelation of a 0.5% (w/v) Aloe pectin solution also occurred in the presence of 1) 0.1% (w/v) silvadene (silver sufadiazine), a poorly soluble anti-bacteria agent commonly used for wound treatment, 2) 0.5% (w/v) hydroxyethyl cellulose (HEC), and 3) 0.5% (w/v) sodium alginate (Keltone HVCR, Kelco). The presence of 0.5% (w/v) HEC or sodium alginate did not influence the efficiency of the in-situ gelation as described in Example 6.

Thus, the fact that the in-situ gelation occurred with these many different agents clearly indicates that the pectin in-situ gel can be used for delivery of a wide range of drug agents.

EXAMPLE 10

Slow Release of a Small Organic Compound from Pectin In-Situ Gels Under

In Vitro Condition

Figure 4:
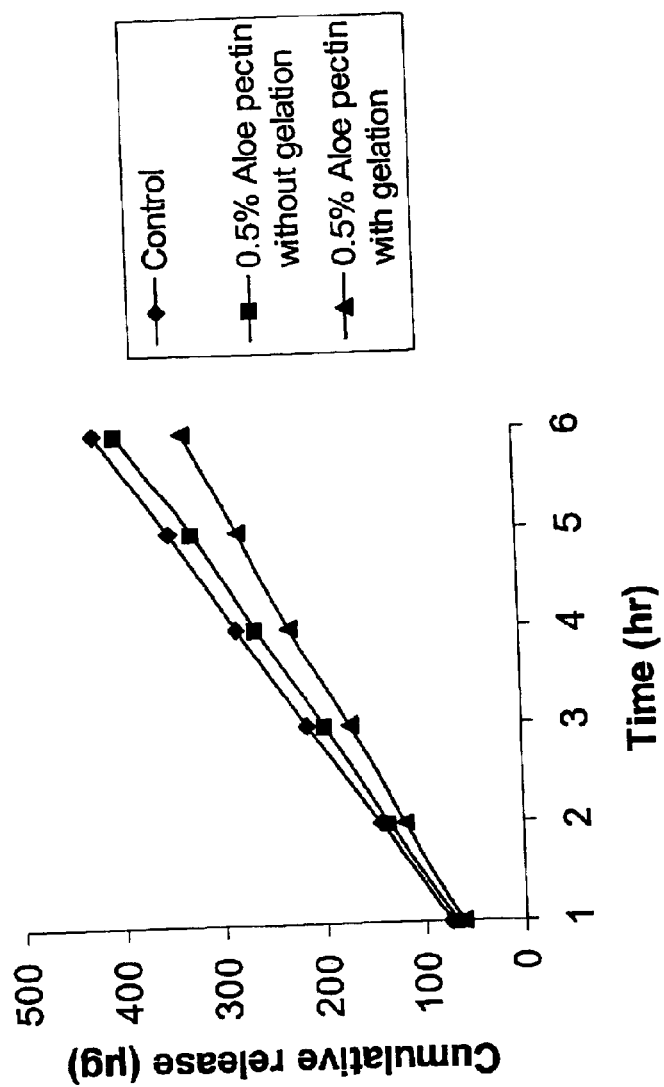
FIG. 4 shows the slow release effect obtained with Aloe pectin in-situ gel using a small organic compound (fast green).

Therapeutic and diagnostic agents vary greatly in molecular weight, from ~100 Da to over 10,000 Da. Generally, the smaller the compound, the more difficult to achieve a slow release effect. Here a small organic compound was chosen as a test model. It is a dye, fast green, which has a molecular weight of 808 and is widely used in the food and pharmaceutical industry. The dye was mixed with Aloe pectin (0.5%, w/v) in saline at a concentration of 1 mg/ml. A 1 mg/ml dye solution in saline only was used as a control. One ml of the dye/pectin preparation or the control was placed into a dialysis tube (1 cm in diameter) with a 12 kDa cut-off. Dialysis tubes with samples were then placed into 25 ml normal calf serum in 30-ml glass tubes. One serum tube receiving the dye/Aloe pectin solution also received EDTA to a final concentration of 10 mM to prevent calcium gelation. The serum tubes containing the samples were then shaken continuously at 100 rpm on a rotatory shaker. A small amount of serum (100 µl) was sampled at various time points. The amount of dye released into the serum was determined by measuring the OD at 620 nm. Serum samples with known amounts of fast green were used to establish the standard curve. The results showed that similar amounts of fast green were released from the control and dye/Aloe pectin with EDTA (without gel formation) and the amount of the dye released from the dye/Aloe pectin without EDTA (with gel formation) was significantly lower ($p<0.05$; student t-test) over the time points measured (FIG. 4). This indicates that the presence of Aloe pectin and its gelation significantly slowed the release of the compound.

EXAMPLE 11

Slow Release of a Small Organic Compound from Pectin In-Situ Gels following

Subcutaneous Injection

To determine if the above observed slow release could be obtained under in vivo conditions, the fast green (1 mg/ml)/ Aloe pectin (0.5%, w/v) in physiological saline or fast green in physiological saline alone was injected subcutaneously into mice. The injection sites (two per sample) were examined 4 hrs later. It was found that with the presence of pectin, in-situ gels were formed, which retained the dye although the color was not as strong as the original preparation prior to injection. In contrast, the injection sites of the control had no color and thus no retained dye. Therefore, the pectin in-situ gel retained the dye and indeed slowed the release under the in vivo condition.

EXAMPLE 12

Local Delivery of bFGF by Aloe Pectin In-Situ Gel

Figure 5:
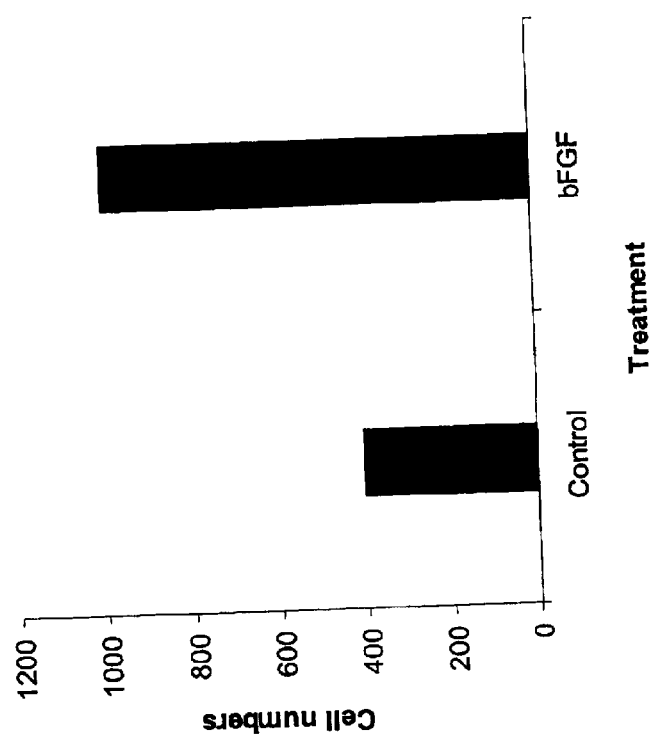
FIG. 5 shows a bar graph representing the relationship between bFGF treatment and cell number in a defined area.

For growth factors to exert local effect on tissues surrounding the administration site, they need to be delivered in a matrix to allow them to be released in a slow or sustained manner. A delivery in saline or buffer alone is not effective in this regard. In this example, a growth factor (bFGF) was used. bFGF (basic fibroblast growth factor or FGF-2) is a growth factor known to stimulate fibroblast proliferation and angiogenesis or blood vessel formation. It was mixed with Aloe pectin (0.5%, w/v) in physiological saline at a concentration of 1–10 µg/ml and then injected subcutaneously into the lower left or right side of abdominal region of mice. One side received the control (pectin alone), and the other side received the bFGF-containing preparation. The in-situ gels from two mice were harvested along with skin at days 5–10 and subjected to fixation in formalin, sectioning, and H&E staining. Two identical areas, at either end of the gel, vertically between the gel surface and the skin muscle layer and horizontally 510 µm inward from the lateral end of the gel were selected, and the cells in these two selected areas from each gel were numerated using the NIH image software. The results showed that the cell number was more than 2 times higher in bFGF-treated than the control (FIG. 5). An increase in blood vessel formation surrounding the gel was also observed at a high bFGF concentration (10 µg/ml). This indicates that bFGF was released from the in-situ gel and exerted its function in the surrounding tissues.

EXAMPLE 13

In-Situ Gelation of a Dried Pectin Composition

A mixture of an Aloe pectin and CMC (0.75% by weight each) and 1.5% CMC prepared in water were lyophilized in weighing trays, separately. The dried materials were cut out as round pads (about 1 cm in diameter and about 3 mm in thickness) and were immersed in a 10 ml of normal calf serum in a petri dish. The Aloe pectin/CMC pad formed a clear gel which remained intact for four days until the experiments were terminated, whereas pads containing CMC alone were dissolved or disappeared in a few hours under the same conditions. Thus, these results show that pectin in a dried form can also form a gel after being immersed in a body fluid.

EXAMPLE 14

Use of Pectin In-Situ Gel for Drug Delivery: Formulation Process

The pectin in-situ gel can be used to provide a physiologically acceptable composition that contains a therapeutic or diagnostic agent and a low concentration of a gelling polymer (pectin) with a pH and osmotic pressure characteristic of the body fluids, and that has the capability to change from liquid to gel upon administration.

The process to prepare a liquid formulation includes the following steps.

1. Pectin is dissolved in sterile water.
2. A buffered or non-buffered saline is prepared.
3. The two solutions are mixed.
4. A physiologically active compound is added to the preparation at step 3. The physiologically active agent may alternatively be added to either solution before mixing.

Besides water and buffered or non-buffered saline or aqueous solution, other pharmaceutically acceptable carriers may also be used, including emulsions such as an oil/water emulsion, adjuvant, various types of wetting agents, tablets, and capsules.

The pH of the formulation is adjusted with suitable buffering agents such as boric acid-sodium borate, sodium phosphate (monobasic)-sodium phosphate (dibasic), and Tris-HCl. Osmotic pressure of the formulation is adjusted to mimic that of body fluids with salts such as NaCl, KCL and $MgCl_2$, and other osmotic adjusting agents such as sorbitol, sucrose, glycerine, and mannitol.

A pharmaceutically acceptable thickener may be added. The thickener can be CMC, HPMC, HEC, alginate, gelatin, dextran, cyclodextrin, or hyaluronic acid.

The formulation may be stored at room temperature or refrigerated (4° C.). If the formulation contains ~0.15 M NaCl, a (sodium) gel is formed when it is stored at 4° C. Prior to application, the gel is allowed to revert back to solution at room temperature. For drug or therapeutic agents that are particulate, prone to aggregate formation, or have a low water solubility such as silvadene (silver sulfadiazine), storage in a gel matrix may be advantageous because it may prevent aggregate or precipitate formation.

Alternatively, the formulation may be prepared in a dried form. A mixture of a pectin and a physiologically active agent in buffered or non-buffered water or saline are lyophilized. Alternatively, a pectin powder and a dry physiologically active agent are blended and compressed into a desired form. The dried form may be used as a pad, a tablet, a capsule, or a powder.

The relative amounts of the physiologically active agent and the pectic substance in the formulation or composition can vary widely dependent on the particular agent to be delivered. In a liquid formulation, the agent can range from about 0.01% to about 50% (w/v) while the pectic substance can range from about 0.01% to about 40% (w/v). In a dried or suspended formulation, either the agent or the pectic substance can range up to over 90% (w/w).

While the preferred compositions or formulations and methods have been disclosed, it will be apparent to those skilled in the art that numerous modifications and variations are possible in light of the above teaching. It should also be realized by those skilled in the art that such modifications and variations do not depart from the spirit and scope of the invention as set forth in the appended claims.

What is claimed is:

1. A method for sustained release of a physiologically active agent to an animal, comprising:
    a) providing a liquid solution or dispersion comprising
        i) a liquid carrier,
        ii) a pectic substance having a degree of methylation of less than 30% and an average molecular weight of greater than $4.6 \times 10^5$ Daltons, in an amount effective to gel the liquid solution or dispersion when applied to the tissues or body fluids of the animal, and
        iii) one or more physiologically active agents; and
    b) applying the liquid solution or dispersion to the tissues or body fluids of the animal to form a gel comprising one or more physiologically active agents in contact with the tissues or body fluids.

2. The method of claim 1 wherein the pectic substance has a degree of methylation of less than about 10%.

3. The method of claim 2 wherein the pectic substance has an average molecular weight of greater than about $0.785 \times 10^6$ Daltons.

4. The method of claim 2 wherein the pectic substance has an average molecular weight of greater than about $1 \times 10^6$ Daltons.

5. The method of claim 4 wherein the pectic substance has a galacturonic acid content of greater than about 90% w/w.

6. The method of claim 4 wherein the pectic substance comprises rhamnose at greater than about 4% by mole.

7. The method of claim 4 wherein the pectic substance comprises 3-methoxy-rhamnose.

8. The method of claim 4 wherein the pectic substance is an aloe pectin.

9. The method of claim 4 wherein the pectic substance comprises from about 0.1% to about 20% of the total weight of the solution or dispersion.

10. The method of claim 4 wherein the pectic substance comprises from about 0.25% to about 2% of the total weight of the solution or dispersion.

11. The method of claim 4 wherein the pectic substance comprises about 0.5% w/v of the solution or dispersion.

12. The method of claim 4 wherein the pectic substance is amidated.

13. The method of claim 1 wherein the solution or dispersion comprises a sodium salt.

14. The method of claim 1 wherein the solution or dispersion is capable of monovalent cation-based gel formation at 4° C.

15. The method of claim 14 wherein the monovalent cation is sodium.

16. The method of claim 4 wherein the solution or dispersion comprises a thickener.

17. The method of claim 4, wherein the solution or dispersion comprises carboxymethylcellulose, hydroxypropylmethylcettular gelatin, dextran, hyaluronic acid, or alginate.

18. The method of claim 4, wherein the carrier comprises water or saline.

19. The method of claim 1 wherein the solution or dispersion is not administered to a mucosal surface.

20. The method of claim 19 wherein the solution or dispersion is administered topically.

21. The method of claim 1 wherein the solution or dispersion is administered to a wound.

22. The method of claim 1 wherein the solution or dispersion is administered to a surgical site.

23. The method of claim 1 wherein the solution or dispersion is administered subcutaneously.

24. The method of claim 1 wherein the solution or dispersion is administered intraperitoneally.

25. The method of claim wherein the solution or dispersion is administered parenterally.

26. The method of claim 1 wherein the solution or dispersion is administered to an organ.

27. The method of claim 1 wherein the solution or dispersion is administered into a tumor.

28. The method of claim 1 wherein the solution or dispersion is administered to a joint cavity.

29. The method of claim 4 wherein the physiologically active agent comprises a pharmacologically active substance, a therapeutic agent, a diagnostic agent, a peptide, a nucleic acid, or a protein.

30. The method of claim 4 wherein the physiologically active agent is a protein.

31. The method of claim 4 wherein the physiologically active agent is a peptide.

32. The method of claim 4 wherein the physiologically active agent is a vaccine.

33. The method of claim 4 wherein the physiologically active agent is a nucleic acid.

34. The method of claim 4 wherein the physiologically active agent is a diagnostic agent.

35. The method of claim 4 wherein the gel provides a sustained release of the physiologically active agent to the tissues or bodily fluids.

36. The method of claim 1 that does not require application of a component comprising cross-linking ions.

37. The method of claim 1 wherein the pectic substance has been filtered to provide a solution which is clearer than that obtained without filtration of the pectic substance.

38. The method of claim 4 wherein the pectic substance has been filtered to provide a solution which is clearer than that obtained without filtration of the pectic substance.

39. The method of claim 4 wherein the physiologically active agent is an anti-bacterial agent.

40. The method of claim 4 wherein the physiologically active agent is silver sulfadiazine.

41. The method of claim 4 wherein the solution or dispersion is administered to a wound.

42. The method of claim 4 wherein the solution or dispersion is administered to a surgical site.

43. The method of claim 4 wherein the solution or dispersion is administered subcutaneously.

44. The method of claim 4 wherein the solution or dispersion is administered intraperitoneally.

45. The method of claim 4 wherein the solution or dispersion is administered parentally.

46. The method of claim wherein the solution or dispersion is administered to an organ.

47. The method of claim 4 wherein the solution or dispersion is administered into a tumor.

\* \* \* \* \*

UNITED STATES PATENT AND TRADEMARK OFFICE
CERTIFICATE OF CORRECTION

PATENT NO. : 6,777,000 B2
DATED : January 13, 2004
INVENTOR(S) : Neuhaus-Steinmetz et al.

It is certified that error appears in the above-identified patent and that said Letters Patent is hereby corrected as shown below:

Column 4,
Line 33, "th an" should read -- than --

Signed and Sealed this

Thirtieth Day of November, 2004

JON W. DUDAS
*Director of the United States Patent and Trademark Office*

UNITED STATES PATENT AND TRADEMARK OFFICE
CERTIFICATE OF CORRECTION

PATENT NO.    : 6,777,000 B2
DATED         : January 13, 2004
INVENTOR(S)   : Neuhaus-Steinmetz et al.

It is certified that error appears in the above-identified patent and that said Letters Patent is hereby corrected as shown below:

Column 4,
Line 33, "th an" should read -- than --

Signed and Sealed this

First Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,777,000 B2
DATED : August 17, 2004
INVENTOR(S) : Ni et al.

It is certified that error appears in the above-identified patent and that said Letters Patent is hereby corrected as shown below:

Title page,
Item [56], References Cited, FOREIGN PATENT DOCUMENTS, please insert the following -- RU 324263   12/23/1971   Aimukhamedova *et al.* --

Column 17,
Line 25, please delete the number "1" and substitute the following -- 4 --
Line 35, please delete the word "carboxyrnethylcellulose" and substitute the Following -- carboxymethycellulose --
Line 35, please delete the word "hydroxypropylmethycellular" and substitute the following -- hydroxpropylmethylcellullose, collagen, --
Line 52, please delete the word "claim" and substitute the following -- claim 1 --

Column 18,
Line 48, please delete the word "claim" and substitute the following -- claim 4 --
Line 52, please insert claim 48 as follows -- 48.  The method of claim 4 wherein the solution or dispersion is administered to a joint cavity. --

Signed and Sealed this

Third Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,777,000 B2
DATED : August 17, 2004
INVENTOR(S) : Ni et al.

It is certified that error appears in the above-identified patent and that said Letters Patent is hereby corrected as shown below:

Title page,
Item [56], References Cited, FOREIGN PATENT DOCUMENTS, please insert the following -- RU 324263    12/23/1971    Aimukhamedova et al. --

Column 17,
Line 25, please delete the number "1" and substitute the following -- 4 --
Line 35, please delete the word "carboxyrnethylcellulose" and substitute the Following -- carboxymethylcellulose --
Line 35, please delete the word "hydroxypropylmethycellular" and substitute the following -- hydroxpropylmethylcellulose, collagen, --
Line 52, please delete the word "claim" and substitute the following -- claim 1 --

Column 18,
Line 48, please delete the word "claim" and substitute the following -- claim 4 --
Line 52, please insert claim 48 as follows -- 48. The method of claim 4 wherein the solution or dispersion is administered to a joint cavity. --

This certificate supersedes Certificate of Correction issued May 3, 2005.

Signed and Sealed this

Twenty-eighth Day of June, 2005

JON W. DUDAS
*Director of the United States Patent and Trademark Office*